United States Patent [19]

Evatt, Jr.

[11] Patent Number: 5,446,583
[45] Date of Patent: Aug. 29, 1995

[54] SURGICAL LIGHT INTERRUPTION DEVICE

[76] Inventor: Clay W. Evatt, Jr., 1135 Cottage Rd., Charleston, S.C. 29412

[21] Appl. No.: 6,832

[22] Filed: Jan. 21, 1993

Related U.S. Application Data

[62] Division of Ser. No. 692,490, Apr. 29, 1991, abandoned.

[51] Int. Cl.⁶ .................. G02B 21/06; G02B 26/02
[52] U.S. Cl. .................................. 359/388; 359/227; 359/385
[58] Field of Search .................. 359/227–236, 359/368, 380–381, 385–389, 477; 351/200–205, 243

[56] References Cited

U.S. PATENT DOCUMENTS

| | | | |
|---|---|---|---|
| 4,324,460 | 4/1982 | Daley | 351/243 |
| 4,560,238 | 12/1985 | Mori | 359/227 |
| 4,561,731 | 12/1985 | Kley | 359/385 |
| 4,657,013 | 4/1987 | Hoerenz et al. | 359/385 |
| 4,940,323 | 7/1990 | Downing | 351/203 |
| 5,299,053 | 3/1994 | Kleinburg et al. | 359/385 |

FOREIGN PATENT DOCUMENTS 156215  7/1986  Japan .................. 359/385

Primary Examiner—Loha Ben
Assistant Examiner—Thong Nguyen
Attorney, Agent, or Firm—B. Craig Killough

[57] ABSTRACT

A surgical light interruption device which interrupts light transmitted to a patient's eye through a surgical microscope at a predetermined interval for a predetermined frequency to reduce light toxicity to the patient's eye during surgery. The device uses an oscillator to intermittently block and allow transmission of light from a light source used in conjunction with the surgical microscope, thereby interrupting light which is transmitted to the patient's eye.

9 Claims, 6 Drawing Sheets 5,446,583

SURGICAL LIGHT INTERRUPTION DEVICE

This is a division of application Ser. No. 07/692,490 filed Apr. 29, 1991 now abandoned.

BACKGROUND OF THE INVENTION

This invention relates generally to medical and surgical devices and is specifically directed to a device which may be used to block or interrupt light received by a patient's eye during eye surgery so as to reduce light toxicity to the eye.

Eye surgery is normally performed with a great amount of light present so that the surgeon can adequately view the patient's eye. Additionally, high voltage lights are present in the operating room. Light is directed in an intense fashion into the patient's eye by illumination presented by the microscope itself. Eye surgery is performed with the aid of a microscope.

It is well established that light is toxic to the eye. Physiologically, the harmful effects of light toxicity are avoided by what is commonly known as blinking. The upper eye lid closes or drops over the eye periodically to intermittently terminate the flow of light to the eye, and to place a tear film over the eye. The average person blinks about 15 times a minute, with the duration of a blink being approximately 0.3 to 0.4 seconds. The average period between blinks is approximately 2.8 seconds for men, and just under 4 seconds for women. The period of blinking may be reduced under certain conditions, such as the presence of bright light.

During surgical procedures on the eye, the eye is held in the open position so that the eye lid cannot close over the eye, or blink. The eye is therefore subject to light toxicity during the surgical procedure, since the eye does not blink for long periods of time.

SUMMARY OF THE PRESENT INVENTION

The present invention provides a device which will intermittently terminate or reduce the flow of light which is directed to the eye during the surgical procedure. The light which is directed into the patient's eye during surgery from a microscope or other source is obscured by the device on an intermittent basis so as to interrupt the flow of light into the eye, and to reduce light toxicity, just as if the patient had blinked.

While it is desirable to intermittently interrupt this flow of light into the patient's eye, such obscuration may be disruptive or distracting to the surgeon. It is therefore desirable to reduce the frequency and duration of this "blink" as much as possible, while effectively reducing toxicity to the eye from exposure to light. Darkening of the field of vision for 0.003 seconds is barely detectable, while darkening the entire visual field for 0.03 seconds by means other than spontaneous blinking is easily noticed.

DESCRIPTION OF THE PREFERRED EMBODIMENTS

Figure 1:
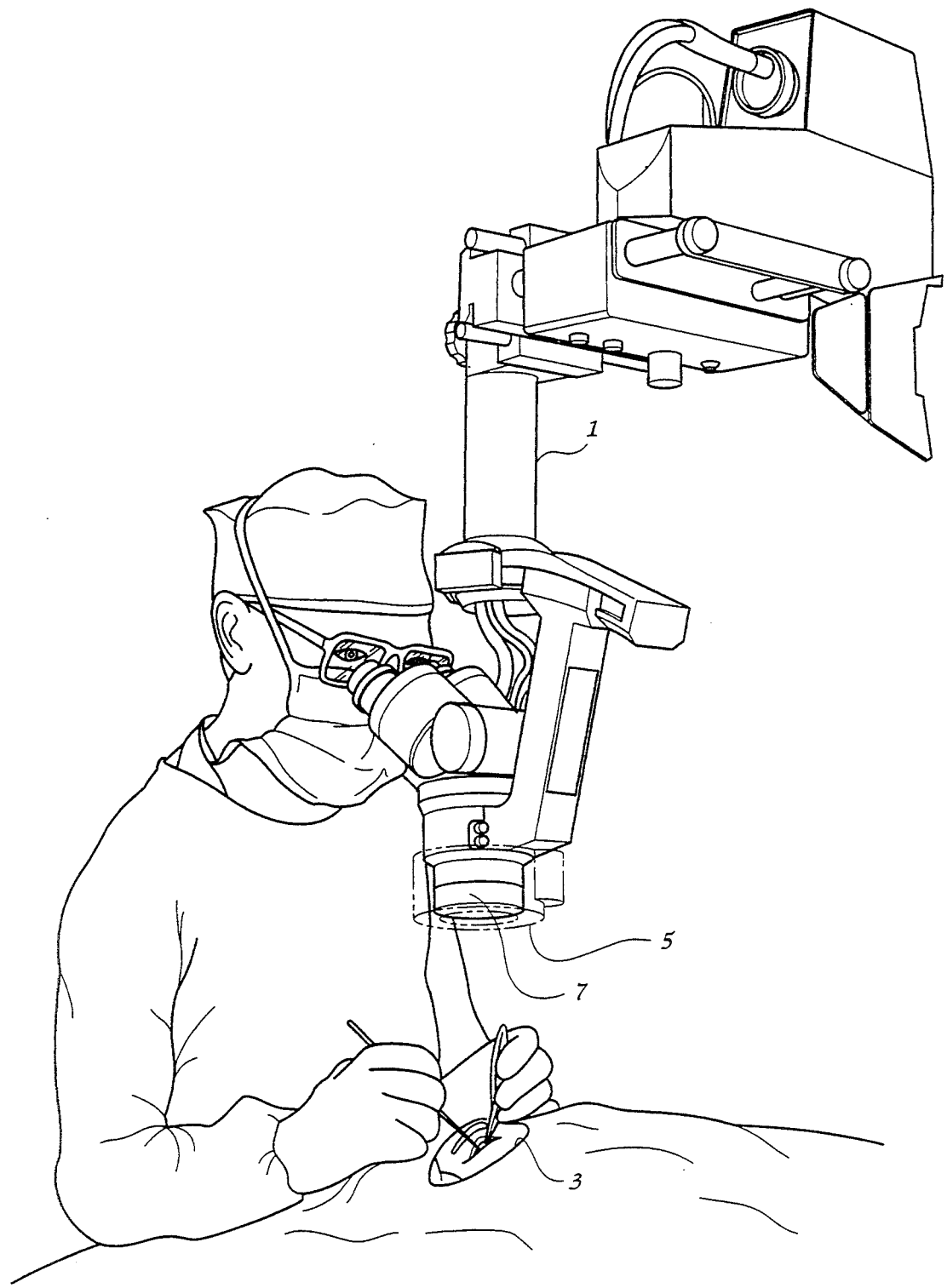
FIG. 1 is an illustration of a surgeon using a surgical microscope, having a light source within the microscope which is directed at a patient's eye. The surgical light interruption device is shown as a phantom, although the device could be otherwise positioned.

FIG. 1 depicts a surgical microscope 1. This microscope is suspended over an operating table to allow proper magnification of the patient's eye during the surgical procedure. The surgeon, who is standing adjacent to the patient, views the patient's eye 3 through the microscope. The microscope is provided with a light source. This light source is generally located away from a magnification means, and is transmitted into the magnification means by an appropriate conveyance means, such as fiber optics. The microscope will have focusing means therein as well.

The present invention periodically interrupts light which is received by the target from the light source. The target is a patient's eye in the preferred embodiment. FIG. 1 shows the device 5 fixed to the microscope between the lens 7 and the target 3. However, light interruption may take place at any point between the light source and the target, or at the light source itself. Accordingly, the device may be positioned in relation to the microscope so as to achieve interruption by means of the light source, or by interrupting the light between the light source and the lens, or by interrupting the light between the light source and the target, or by interrupting the light between the lens and the target.

Figure 9:
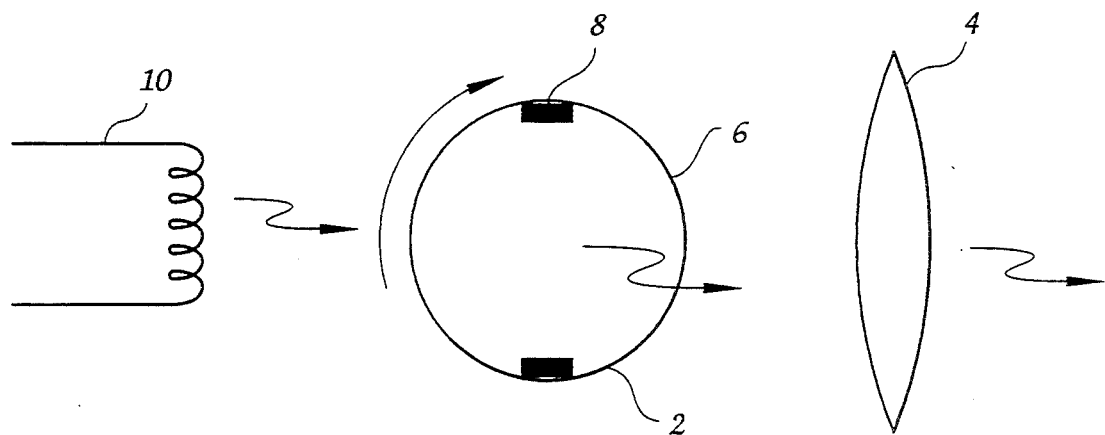
FIG. 9 shows a continuously revolving means 2 which uses alternating transparent 6 and opaque 8 areas to alternately block and allow light from the light source 10 to pass through a lens.
Figure 10:
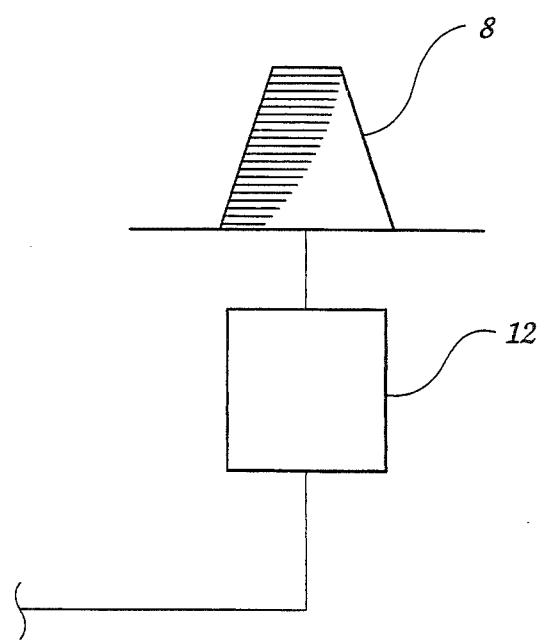
FIG. 10 is an elevation view of a variable speed motor 12 connected to the revolving mean 2 of FIG. 9.

One embodiment is a revolving shutter. FIG. 9. A revolving wheel 2 is placed between the surgical microscope light source and the target. The revolving wheel is characterized by alternating transparent areas 6 or voids and one or more opaque surfaces 8. In this embodiment, as the wheel turns about its axis, the transparent areas 6 or voids allow light from the light source 10 to pass to the lens 4, while the opaque areas 8 block the light, preventing the light from passing to the lens and into the patient's eye, or target.

By varying the rotational speed of the wheel, the frequency of blocking of light from reaching the patient's eye is varied. In the preferred embodiment, the revolving wheel 2 is powered by a variable speed electric motor 12. Control means, such as a rheostat, may be used to allow the speed of the motor to be selectively changed within acceptable ranges, as desired by the surgeon. Means could be provided to increase the relative area of the opaque areas(s) to vary the period of obscuration.

Figure 5:
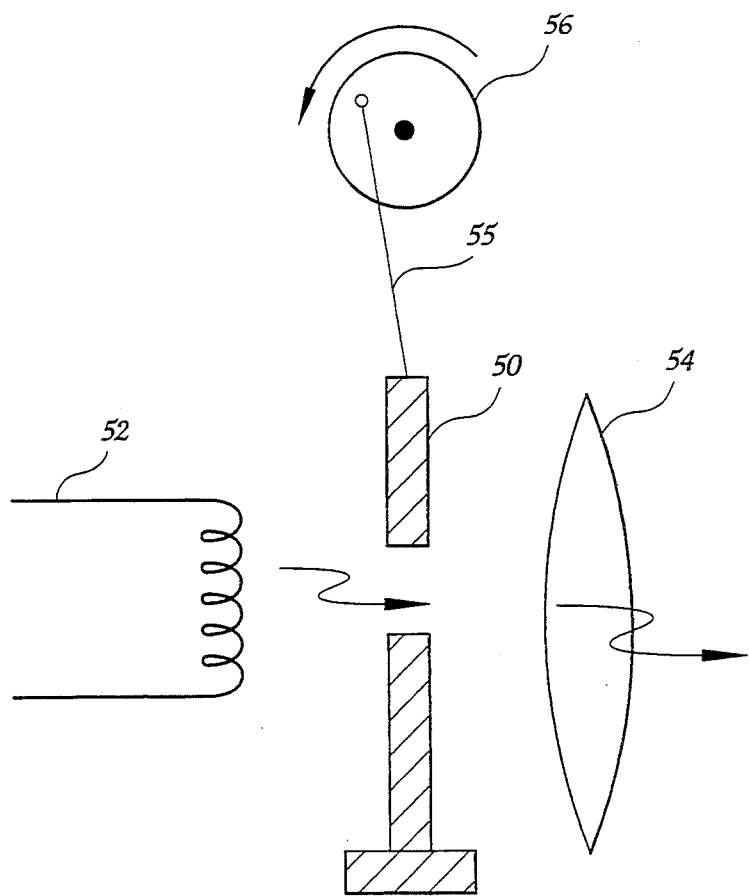
FIG. 5 shows the front view of the mechanical shutter 50 of FIG. 4 which is used to intermittently block light from a light source 52.

A mechanical shutter is used to intermittently obstruct light emanating from the surgical microscope as shown in FIG. 5. The mechanical shutter 50 is located at the desired point between the light source 52 of the surgical microscope and the target. Means is provided to alternately pull the mechanical shutter away from its position of blockage of the light source, and to then replace the shutter so as to block the light in an intermittent fashion.

In this embodiment, the mechanical shutter works in a sliding fashion. The shutter slides in one direction so as to allow transmission of the light from the light source, and then slides in an opposite direction so as to block light from the light source.

A rotating wheel 56 is powered by a variable speed motor 58. The speed of the motor may be controlled by the surgeon by means of a rheostat, or otherwise. One end of a linkage 55 is attached to the rotating wheel 56, with the opposite end of the linkage attached to a portion of the mechanical shutter 50. As the motor rotates, the mechanical shutter slides so as to be pulled away from its blocking position, allowing light to pass through the shutter, with the shutter then being replaced as the wheel rotates so as to block the light, which in this illustration, then passes to the lens 54.

Figure 7:
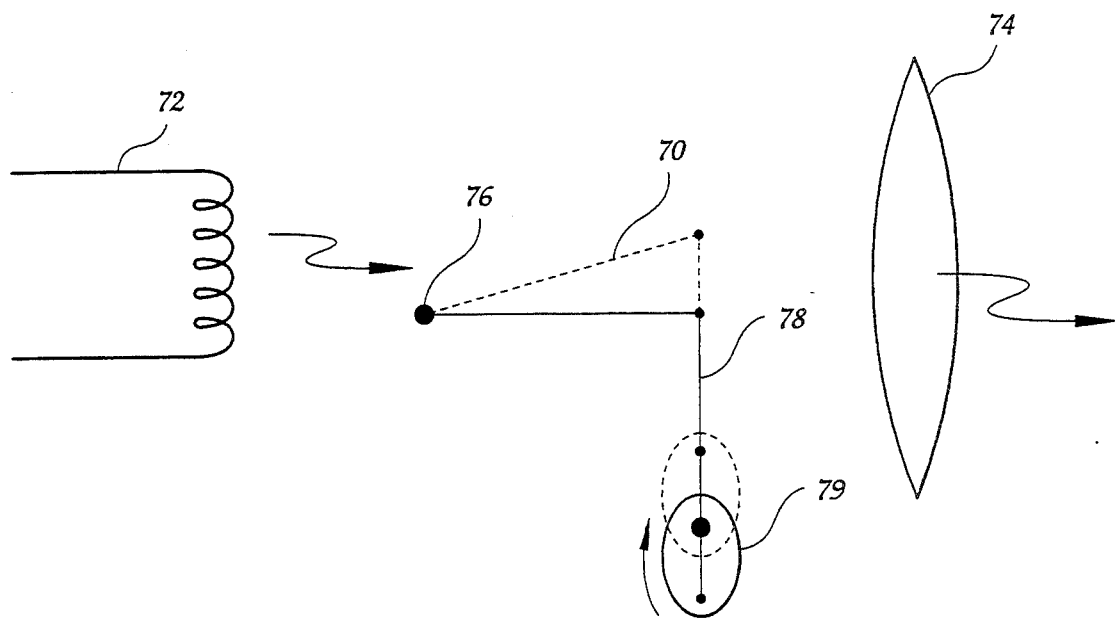
FIG. 7 is a plane 70 which is connected by a linkage 78 to a cam 79 which is rotated to as to cause the plane to block light from a light source 72.

A movable plane 70, which could be reflective or opaque, is placed between a light source 72 of a surgical microscope and a target of the surgical microscope to intermittently obstruct light as it travels to or from the lens 74 and to the patient's eye. The plane, which could be a mirror, is alternately moved by an actuation means to block the light source, and is then removed from the blocking position. FIG. 7.

In this embodiment, a mirror 70 is hinged 76 at one end. When the device is in its open position so as to allow light to travel to the target, the plane of the mirror may be generally parallel to the direction of travel of light between the light source and the lens. An actuation means is used to push the hinged mirror between the light source and the lens to block the light from the lens. In the preferred embodiment, a linkage 78 is attached to the end of the mirror opposite the hinge, and the opposite end of the linkage is attached to a cam 79. A variable speed motor is used to rotate the cam, which causes the mirror to alternately move into position to block the light, then withdraw. The frequency of blockage may be changed by varying speed of the motor, such as by rheostat means.

Figure 2:
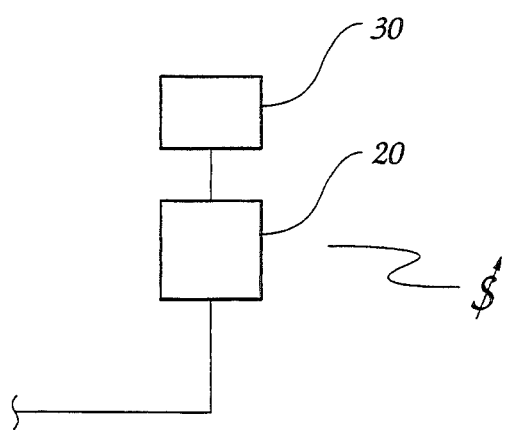
FIG. 2 shows a variable speed motor 20 connected to rotating prism 30 which selectively directs light to a target.
Figure 3:
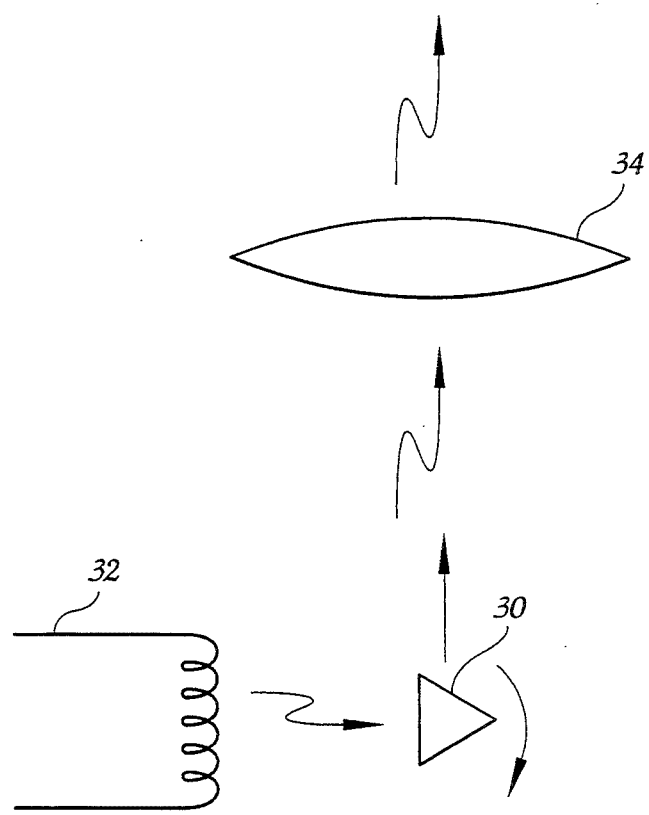
FIG. 3 is a rotating prism 30 which receives light from a light source, and directs it through a lens of a microscope 34 to a target.
Figure 4:
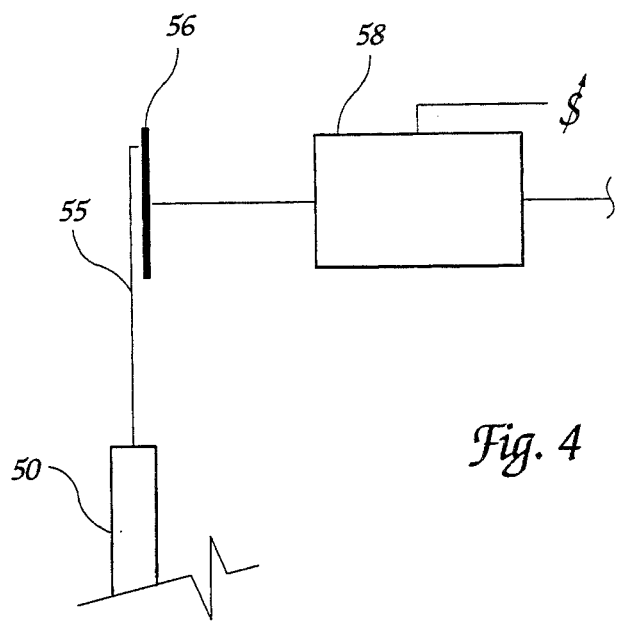
FIG. 4 demonstrates a variable speed motor 58, and actuation means 55, 56 used to operate shutter 50.

A prism may be rotated in front of a light source or lens so as to direct light emanating from the light source to the target. FIG. 3 shows a rotating prism 30 which directs light from a light source 32 to a lens 34 of a surgical microscope. FIG. 2 shows a variable speed motor 20 which is used to actuate and rotate the prism 30.

Figure 6:
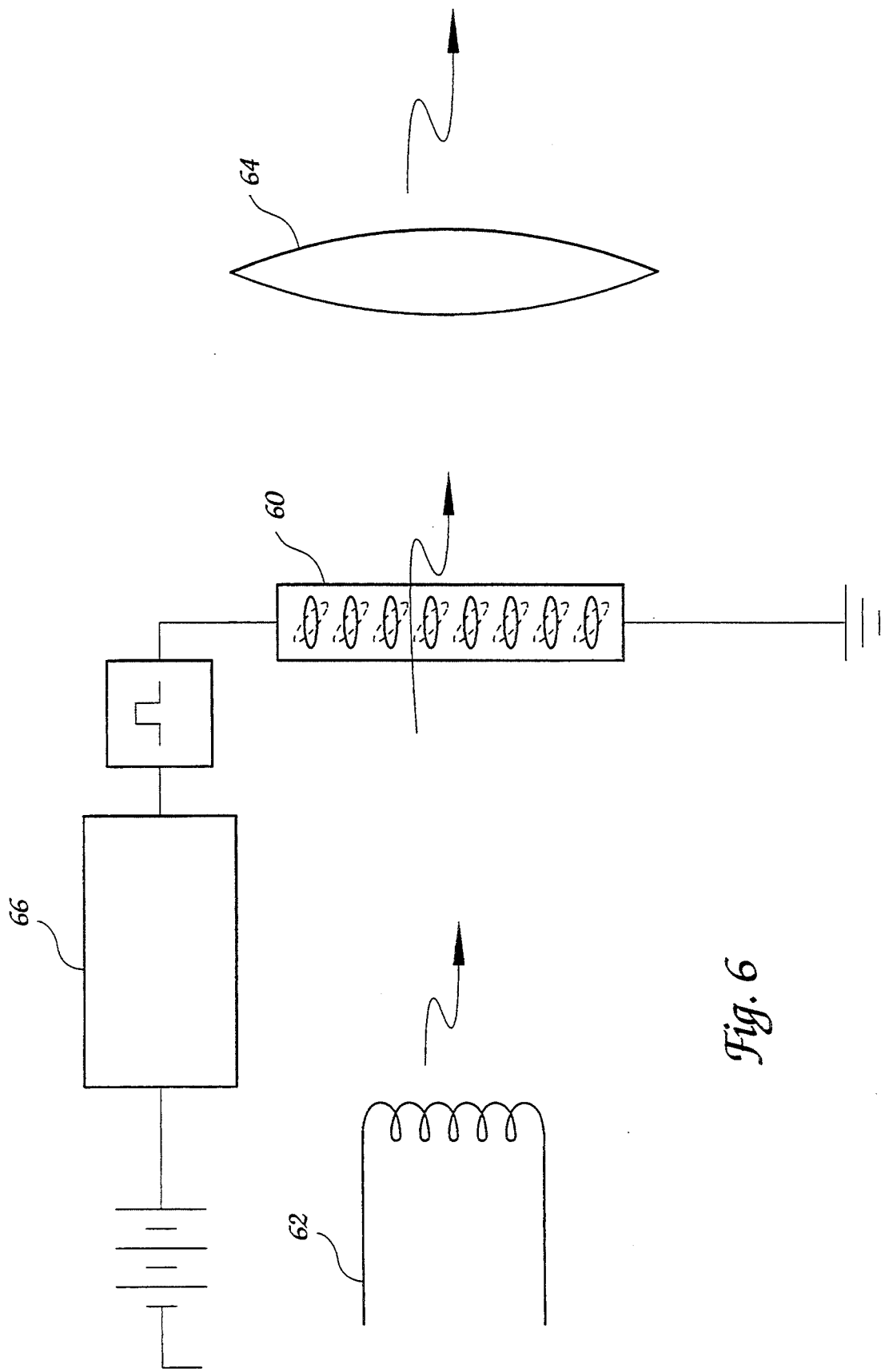
FIG. 6 shows a liquid crystal shutter 60 which uses an oscillator 66 to switch the liquid crystal means to block light from the light source 62.

A liquid crystal shutter 60 is placed between a light source 62 of a surgical microscope and a target to intermittently allow and prevent light from striking the patient's eye. FIG. 6. A liquid crystal shutter means is provided which will normally allow light to pass through it. The application of current, which may be direct current, to the liquid crystal shutter causes the light to be blocked as it travels from the light source, preventing the light source from reaching the patient's eye, and as shown, the lens 64. An adjustable frequency oscillator 66 may be used to selectively allow or prevent the current from being applied to the liquid crystal shutter. This adjustable frequency oscillator may be adjusted so as to vary the frequency at which a current is applied to the shutter, as well as the period of duration of the current application.

Figure 8:
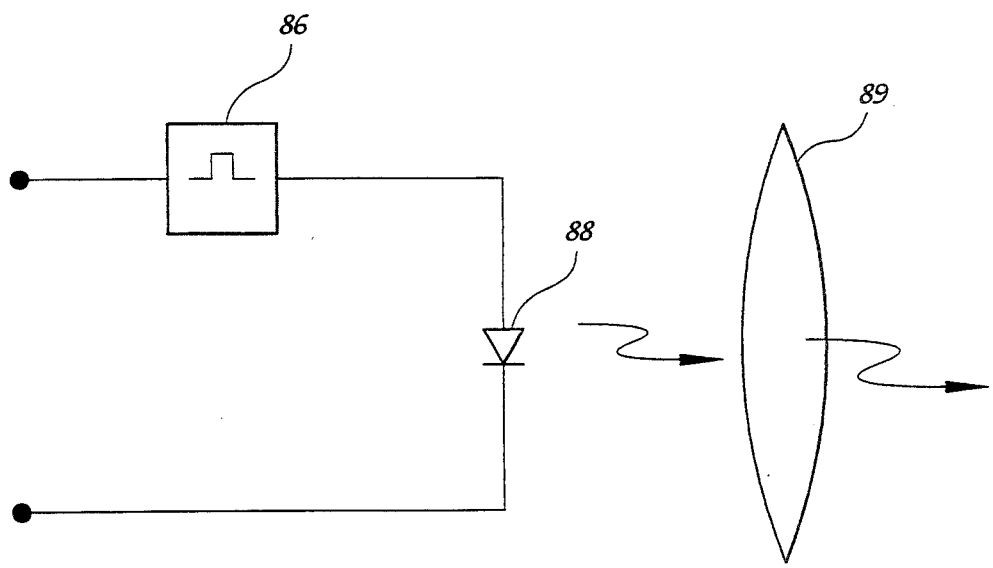
FIG. 8 shows an adjustable oscillator 86 which causes a light source, such as a diode 88, to intermittently produce light passing through a lens 89 of a surgical microscope.

FIG. 8 shows a light source as a semiconductor 88 which is controlled by an oscillator 86 so as to provide illumination to the lens on an intermittent basis using the semiconductor as a light source. The frequency and period of the illumination of light source may be controlled so as to provide the blinking effect.

In this embodiment, a current is applied to semiconductor 88, or to a gas, such as xenon gas. As the xenon gas breaks down, it emits light. When the voltage is terminated, the gas ceases to yield light, thereby terminating the illumination of the lens.

As shown, the current may be supplied by a power source to an adjustable frequency oscillator 86. The adjustable frequency oscillator supplies voltage to a semiconductor, which could be a diode 88, on an intermittent basis so as to modulate the light output. The semiconductor could be replaced with a gas discharge light source. The adjustable frequency oscillator allows the frequency of the switching on and off to be predetermined, as well as the period during which the light source is on or off. This light source may be used in combination with the remaining embodiments enclosed herein to control the period and frequency of the blinking effect.

What is claimed is:

1. A device for periodically interrupting a light source used during surgery, comprising:
   a. a microscope having magnification means therein;
   b. a light source which directs light through said magnification means to a target;
   c. an oscillating means; and
   d. a shutter means which is connected to said oscillating means and is controlled by said oscillating means, wherein said shutter means has at least one shutter which is opened periodically by said oscillating means to allow light to pass through said shutter, and said shutter is closed periodically by said oscillating means to prevent light from passing through said shutter, and wherein said shutter is located between said light source and said target.

2. A device for periodically interrupting a light source used during surgery as described in claim 1, wherein said shutter is a liquid crystal shutter.

3. A device for periodically interrupting a light source used during surgery as described in claim 1, wherein said oscillating means is a wheel.

4. A device for periodically interrupting a light source used during surgery as described in claim 3, wherein said shutter means is connected to said wheel by a linkage.

5. A device for periodically interrupting a light source used during surgery as described in claim 1, wherein said oscillating means is an adjustable frequency oscillator.

6. A device for periodically interrupting a light source used during surgery as described in claim 5, wherein said shutter is a liquid crystal shutter.

7. A device for periodically interrupting a light source used during surgery as described in claim 1, wherein said oscillating means is a cam.

8. A device for periodically interrupting a light source used during surgery as described in claim 1, wherein said oscillating means is connected to said shutter means by a linkage.

9. A device for periodically interrupting a light source used during surgery, comprising:
 a. a microscope having magnification means therein;
 b. a light source which directs light through said magnification means to a target;
 c. an oscillating means; and
 d. a shutter means which is connected to said oscillating means and is controlled by said oscillating means, wherein at least one surface of said shutter which is located in a path of said light from said light source to said target is reflective.

* * * * *